United States Patent
Gemma et al.

(10) Patent No.: US 8,761,341 B2
(45) Date of Patent: Jun. 24, 2014

(54) X-RAY IMAGING SYSTEM

(75) Inventors: Kohei Gemma, Kanagawa (JP);
Takehisa Ono, Kanagawa (JP); Noriaki Ida, Kanagawa (JP); Takeshi Kamiya, Kanagawa (JP)

(73) Assignee: FUJIFILM Corporation, Tokyo (JP)

(*) Notice: Subject to any disclaimer, the term of this patent is extended or adjusted under 35 U.S.C. 154(b) by 275 days.

(21) Appl. No.: 13/213,270

(22) Filed: Aug. 19, 2011

(65) Prior Publication Data

US 2012/0051511 A1 Mar. 1, 2012

(30) Foreign Application Priority Data

Aug. 31, 2010 (JP) ................................. 2010-194082

(51) Int. Cl.
*H05G 1/56* (2006.01)
(52) U.S. Cl.
USPC ............................................ 378/114; 378/91
(58) Field of Classification Search
USPC ............... 378/91, 98, 98.2, 114–118
See application file for complete search history.

(56) References Cited

U.S. PATENT DOCUMENTS 4,160,906 A * 7/1979 Daniels et al. ................... 378/97

FOREIGN PATENT DOCUMENTS

| JP | 07-031609 A | 2/1995 |
| JP | 2003033342 A | 2/2003 |
| JP | 2004171386 A | 6/2004 |
| JP | 2008-142111 A | 6/2008 |

OTHER PUBLICATIONS

Notification of Reasons for Refusal, dated Jan. 14, 2014, issued in corresponding JP Application No. 2010-194082, 6 pages in English and Japanese.

* cited by examiner

*Primary Examiner* — Jurie Yun
(74) *Attorney, Agent, or Firm* — Sughrue Mion, PLLC

(57) ABSTRACT

The X-ray imaging system includes an X-ray source, a console, an X-ray controller for controlling an operation of the X-ray source according to X-ray control parameters set by the console, and an X-ray detector for detecting X-ray radiated from the X-ray source and transmitted through a subject and thereby outputting an image signal of an X-ray image of the subject. The console includes an input unit for entering the X-ray control parameters, which are information for controlling the operations of the X-ray source and a controller for holding setting range information representing an allowable range of values of the X-ray control parameters and making a judgment as to whether values of the entered X-ray control parameters are settable values according to the setting range information and informing an user of the console of the judgment.

15 Claims, 6 Drawing Sheets

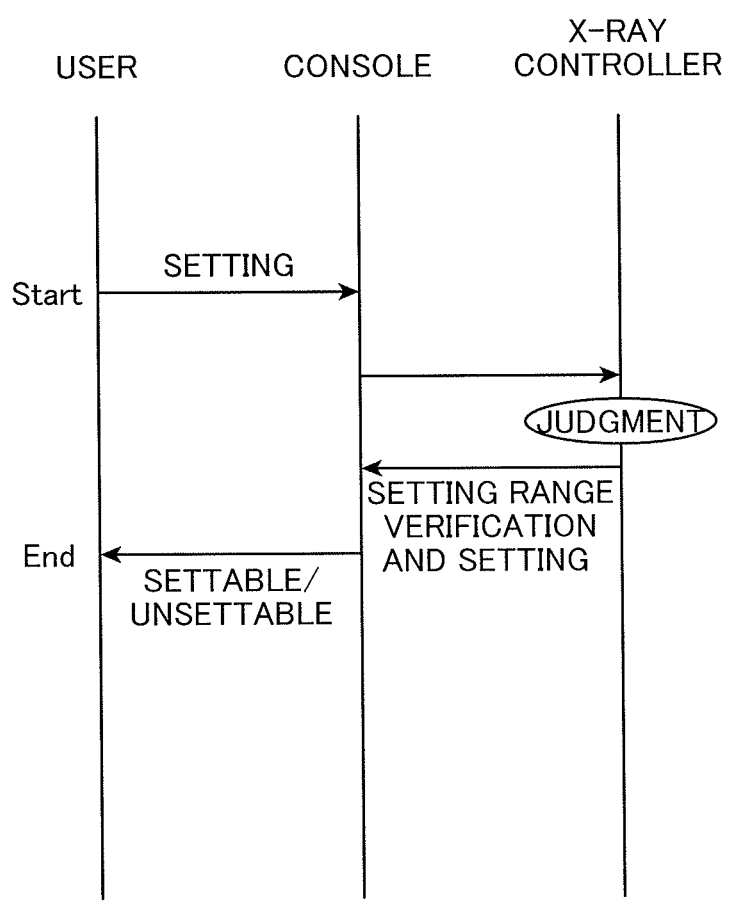

X-RAY IMAGING SYSTEM

BACKGROUND OF THE INVENTION

The present invention relates to an X-ray imaging system for irradiating a subject (patient) with X-ray and detecting the X-ray transmitted through the subject to produce an X-ray image and to a console and an input terminal used for the X-ray imaging system.

FIG. 5 is a block diagram illustrating an example of a configuration of a conventional X-ray imaging system. An X-ray imaging system 50 illustrated in that figure is used to produce an X-ray image of a subject and comprises an imaging apparatus and a console 45.

The imaging apparatus 52 comprises an X-ray source 56 for radiating X-ray, an X-ray controller 58 for controlling the operation of the X-ray source 56 and an input unit 60 thereof, an X-ray detector 62 for detecting X-ray transmitted through the subject, and an imaging table 64 for positioning the subject. The console 54 comprises a controller 66 for controlling the operation of the whole X-ray imaging system 50 and an input unit 68 thereof.

In the imaging system 52, the input unit 60 is connected to the X-ray controller 58, which in turn is connected to the X-ray source 56. In the console 54, the input unit 68 is connected to the controller 66. The X-ray controller 58, the X-ray detector 62, the imaging table 64, and the controller 66 of the console 54 are connected to each other via a network 70.

With the conventional X-ray imaging system 50, a user (e.g., an X-ray imaging technician) enters X-ray control parameters or information for controlling the operation of the X-ray source 56 through the input unit 60 of the X-ray controller 58 and console control parameters or information for controlling the operation of the console 54 through the input unit 68 of the console 54.

The X-ray controller 58 holds first setting range information representing an allowable range of values of the X-ray control parameters, based on which judgment is made as to whether the values of the X-ray control parameters entered through the input unit 60 are settable values. Upon judging that the values are settable, the X-ray controller 58 sets the entered X-ray control parameters in the X-ray controller 58.

The controller 66 of the console 54 holds second setting range information representing an allowable range of values of the console control parameters, based on which judgment is made as to whether the values of the console control parameters entered through the input unit 68 are settable values. Upon judging that the values are settable, the controller 66 of the console 54 sets the entered console control parameters in the controller 66.

Control provided by the controller 66 of the console 54 ensures that when the values of the console control parameters are judged to be settable, the operation of the individual components of the X-ray imaging system 50 is controlled based on the console control parameters.

When the user pushes an exposure button at a time of X-ray image acquisition, the X-ray controller 58 controls the operation of the X-ray source 56 according to the X-ray control parameters. Thus, the X-ray source 56 radiates X-ray, and the X-ray transmitted through the subject is detected by the X-ray detector 62 to acquire an X-ray image. The acquired X-ray image is entered in the controller 66 of the console 54, undergoes image processing, etc., and is, for example, displayed on a monitor.

When the values of the X-ray control parameters entered through the input unit 60 and the values of the console control parameters entered through the input unit 68 are judged to be not settable, the user makes settings over again.

However, the X-ray imaging system 50 requires the user to enter the console control parameters from the input unit 68 of the console 54 and enter the X-ray control parameters from the input unit 60 of the X-ray controller 58. Therefore, whenever the X-ray control parameters or the console control parameters are judged to be unsettable values, the console 54 and the X-ray controller 58 needed to exchange data as illustrated in FIG. 6 to set new parameters.

Thus, the X-ray imaging system 50 had problems that imaging operations are complicated and hence reduce efficiency in imaging operations. The system also had a problem that it required a long time to accomplish imaging procedure, that is, the subject was required to wait a long period of time and bear an increased strain.

Among prior art literature describing X-ray imaging systems comprising an X-ray source, an X-ray controller, and an X-ray detector are, for example, JP 07-31609 A and JP 2008-142111 A. However, there is no prior art literature directly related to the present invention.

SUMMARY OF THE INVENTION

An object of the present invention is to provide a console, an input terminal, and an X-ray imaging system using them, whereby imaging operations for setting the X-ray control parameters and the console control parameters can be simplified and the imaging efficiency can be increased.

In order to attain the object described above, the present invention provides a console used for an X-ray imaging system for acquiring an X-ray image of a subject to control an operation of the X-ray imaging system in its entirety, the console comprising:

an input unit for entering X-ray control parameters, which are information for controlling an operation of an X-ray source; and a controller holding first setting range information representing an allowable range of values of the X-ray control parameters, the controller making a judgment as to whether the values of the X-ray control parameters entered through the input unit are settable values according to the first setting range information and informing a user of the console of the judgment.

Also, the present invention provides an X-ray imaging system comprising:

an X-ray source for radiating X-ray;
the console described above;
an X-ray controller for controlling an operation of the X-ray source according to X-ray control parameters that are set when the values of the entered X-ray control parameters are judged by the controller of the console to be settable values; and
an X-ray detector for detecting X-ray radiated from the X-ray source and transmitted through a subject and thereby outputting an image signal of an X-ray image of the subject.

Also, the present invention provides an input terminal used for an X-ray imaging system for acquiring an X-ray image of a subject, comprising:

an input unit for entering X-ray control parameters, which are information for controlling an operation of an X-ray source, and console control parameters, which are information for controlling an operation of a console for controlling an operation of the X-ray imaging system in its entirety; and a controller for holding first setting range information representing an allowable range of values of the X-ray control parameters and second setting range information representing an allowable range of values of the console control parameters, the controller making a judgment as to whether the values of the X-ray control parameters entered through the input unit are settable values according to the first setting range information, making a judgment as to whether the values of the console control parameters entered through the input unit are settable values according to the second setting range information, and informing a user of the input terminal of these judgments.

And also, the present invention provides an X-ray imaging system comprising:

an X-ray source for radiating X-ray;

the input terminal described above;

a console for controlling an operation of the X-ray imaging system in its entirety according to the console control parameters that are set when the values of the entered console control parameters are judged by the input terminal to be settable values;

an X-ray controller for controlling an operation of the X-ray source according to X-ray control parameters that are set when the values of the entered X-ray control parameters are judged by the input terminal to be settable values; and an X-ray detector for detecting X-ray radiated from the X-ray source and transmitted through a subject and thereby outputting an image signal of an X-ray image of the subject.

The X-ray imaging system of the invention enables setting of the X-ray control parameters in the X-ray controller simply by entering the X-ray control parameters from the input unit of the console and allows the controller of the console to make a judgment as to whether the X-ray control parameters are settable values and inform the user of the judgment. Therefore, the X-ray imaging system of the invention permits simplification of the imaging operations and improvement in imaging efficiency. Further, the X-ray imaging system of the invention can shorten the time during which the subject is required to wait until an X-ray image acquisition is completed, thus reducing the strain on the subject.

BRIEF DESCRIPTION OF DRAWINGS

FIG. 6 is a conceptual view illustrating an operation of the X-ray imaging system of FIG. 5.

DETAILED DESCRIPTION OF THE INVENTION

The console, the input terminal, and the X-ray imaging system of the invention will be described in detail based on preferred embodiments illustrated in the attached drawings.

Figure 1:
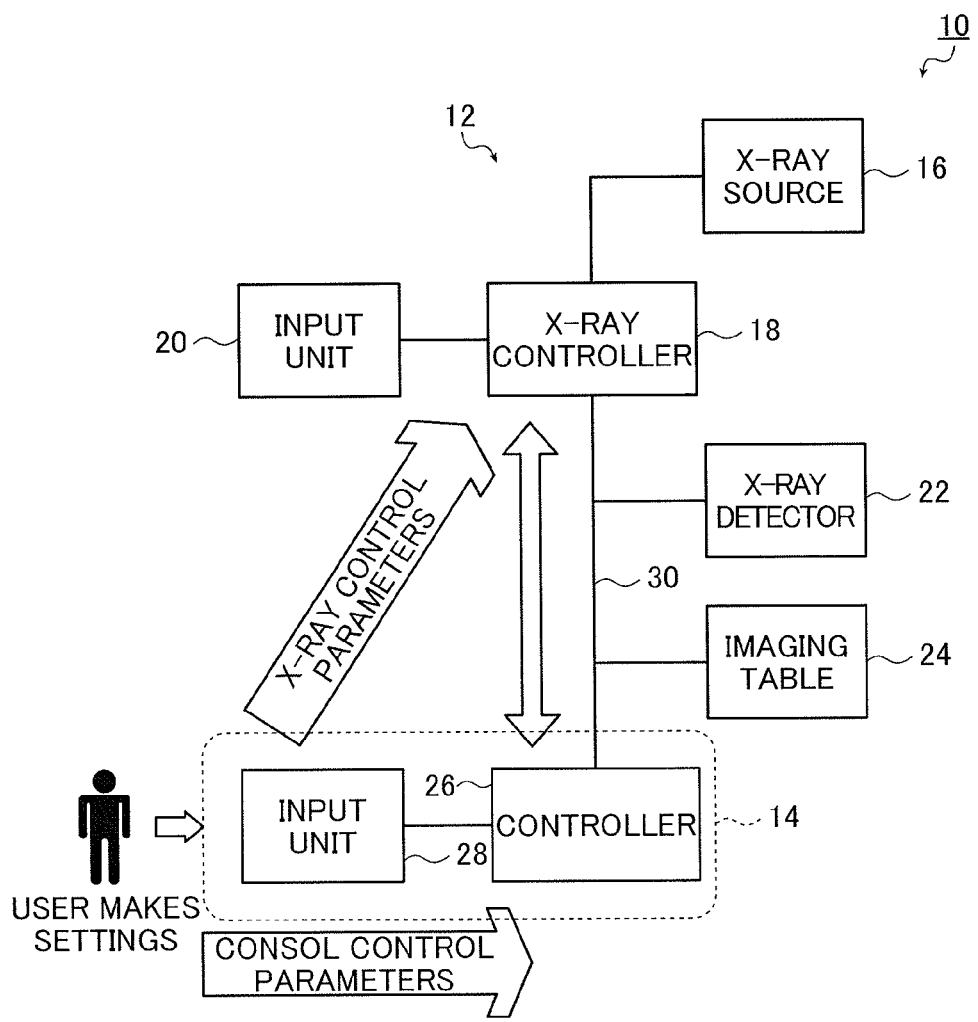
FIG. 1 is a block diagram illustrating a first embodiment representing a configuration of the X-ray imaging system of the invention.

FIG. 1 is a block diagram illustrating the first embodiment representing a configuration of the X-ray imaging system of the invention. An X-ray imaging system 10 illustrated in that figure comprises an imaging apparatus 12 and a console 14.

The imaging apparatus 12 comprises an X-ray source 16, an X-ray controller 18 and an input unit 20 thereof, an X-ray detector 22, and an imaging table 24. The input unit 20 is connected to the X-ray controller 18, which in turn is connected to the X-ray source 16. The X-ray controller 18, the X-ray detector 22, the imaging table 24, and the controller 26 of the console 14 described later are connected to each other via a network 30.

Under the control of the X-ray controller 18, the X-ray source 16 radiates X-ray having a given intensity for a given time period at a time of X-ray image acquisition. That is, the X-ray source 16 radiates a given irradiance (dose) of X-ray.

The X-ray controller 18 controls the operation of the X-ray source 16 according to the X-ray control parameters set by the controller 26 of the console 14 described later.

The input unit 20 is an input means for entering various information in the X-ray controller 18. Although this embodiment does not use the input unit 20, the input unit 20 may be used to enter the X-ray control parameters.

The X-ray detector 22 detects the X-ray radiated from the X-ray source 16 and transmitted through the subject and outputs an image signal of an X-ray image of the subject. The X-ray detector 22 may be, for example, a cassette for X-ray image acquisition. The cassette comprises an X-ray imaging means such as an X-ray imaging film, an IP (imaging plate), and an FPD (flat panel detector).

The imaging table 24 is a table for positioning the subject during an X-ray image acquisition procedure. The imaging table 24 may be a mere positioning table for X-ray image acquisition using the X-ray detector 22. The imaging table 24 may be of a fixed type such that an X-ray detector is incorporated in a standing-position imaging table or a lying position imaging table or of a portable type to which an X-ray detector is attached at a time of X-ray image acquisition.

The console 14 controls the operation of the entire X-ray imaging system 10 and comprises, for example, a monitor (not shown) for displaying various information in addition to the controller 26 and an input unit 28 thereof. The input unit 28 and the monitor are connected to the controller 26, and the controller 26 is connected to the network 30 as described earlier.

The input unit 28 is an input means for entering in the controller 26 various information including X-ray control parameters or information for controlling the operation of the X-ray source 16 and the console control parameters or information for controlling the operation of the console 14.

The X-ray control parameters may be exemplified by a tube voltage and a tube current of the X-ray source 16, an X-ray irradiation time, AEC (automatic exposure control), and the size of a patient. The console control parameters may be exemplified by patient information, a mode of X-ray imaging (standing position, lying position), an imaging site, a size of X-ray radiation exposure field, an imaging reference position, and an image processing condition.

The controller 26 holds the first setting range information representing an allowable range of values of the X-ray control parameters and the second setting range information representing an allowable range of values of the console control parameters. The controller 26 makes a judgment as to whether the values of the X-ray control parameters entered through the input unit 28 are settable values according to the first setting range information and also makes a judgment as to whether the values of the console control parameters entered through the input unit 28 are settable values according to the second setting range information and informs the user of the judgments through the monitor or the like. The controller 26 sets the entered X-ray control parameters in the X-ray controller 18 when they are judged to be settable values, and sets the entered console control parameters in the controller 26 of the console 14 when they are judged to be settable values.

Next, the operation of the X-ray imaging system 10 will be described.

In the description to follow, it is supposed that third setting range information, which is original information of the first setting range information, is held in the X-ray controller 18.

Figure 2:
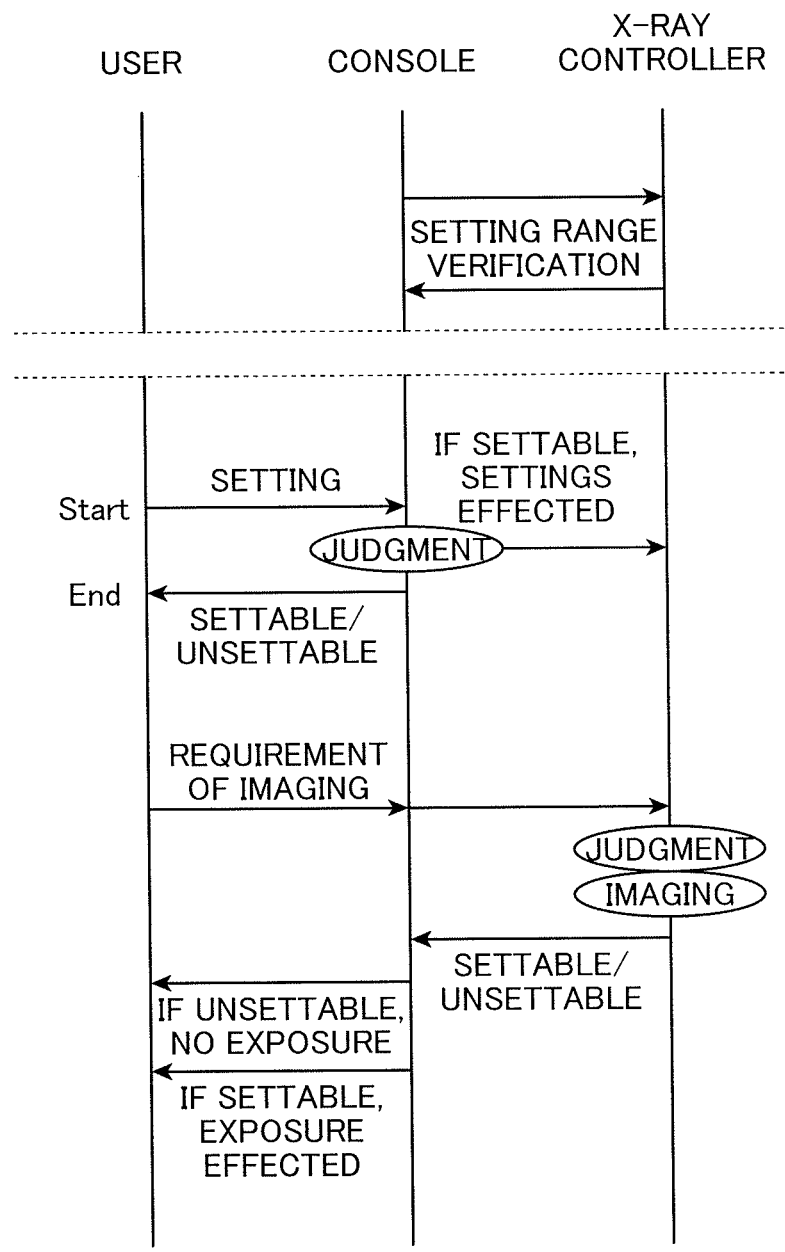
FIG. 2 is a conceptual view illustrating an operation of the X-ray imaging system of FIG. 1.

As illustrated in FIG. 2 showing a concept of the operation, when, for example, the power of the X-ray imaging system 10 is turned on every morning, first the console 14 judges whether the values of the first setting range information held in the controller of the console 14 agree with the values of the third setting range information held in the X-ray controller 18 (setting range verification). When they are judged to disagree, the values of the first setting range information are reset to the same values as the values of the third setting range information.

This ensures that even when the first setting range information held in the controller 26 has become unsettable values for some reason, the values are renewed and corrected each time the power is turned on and thus an inappropriate X-ray exposure may be prevented.

Then, the user (e.g., an X-ray imaging technician) enters (sets) the X-ray control parameters and the console control parameters in the X-ray imaging system 10 through the input unit 28 of the console 14.

Upon entry of the X-ray control parameters and the console control parameters, the controller 26 judges whether the values of the entered X-ray control parameters are settable values according to the first setting range information and also judges whether the values of the entered console control parameters are settable values according to the second setting range information.

When the controller 26 judges that both the values of the entered X-ray control parameters and the entered console control parameters are settable values, the user is informed that the values are settable values (setting OK). Then the entered X-ray control parameters are set in the X-ray controller 18, while the entered console control parameters are set in the controller 26 of the console 14.

When the controller 26 judges that the values of the entered X-ray control parameters, the entered console control parameters, or both are judged to be unsettable values, the user is informed that the values are unsettable values (UNSETTABLE). Accordingly, the user repeats the operation starting with the entry of the X-ray control parameters or the console control parameters or both judged to be unsettable values.

Control provided by the controller 26 of the console 14 ensures that when the values of the console control parameters are judged to be settable, the operations of the individual components of the X-ray imaging system 10 are controlled according to the console control parameters.

When informed that both the X-ray control parameters and the console control parameters are settable values, the user pushes the exposure button (requirement of image acquisition).

Upon push of the exposure button, the X-ray controller 18 makes a judgment as to whether the X-ray control parameters set by the controller 26 of the console 14 are settable values according to the third setting range information before and preferably immediately before X-ray image acquisition, and the user is informed of the judgment. When the values are judged to be unsettable values (UNSETTABLE), X-ray exposure is stopped.

This ensures that even when the values of the X-ray control parameters set in the X-ray controller 18 have become unsettable values for some reason, an inappropriate X-ray exposure may be prevented by detecting that fact before image acquisition.

When, on the other hand, the values are judged to be settable (SETTABLE), the X-ray controller 18 controls the operation of the X-ray source 16 according to the X-ray control parameters to cause the X-ray source 16 to irradiate the subject with X-ray. Then, the X-ray transmitted through the subject positioned by the imaging table 24 is detected by the X-ray detector 22 to acquire an X-ray image. The image signal of the acquired X-ray image is entered in the controller 26 of the console 14, undergoes image processing, etc., and is, for example, displayed on the monitor.

With the X-ray imaging system 10, merely entering the X-ray control parameters and the console control parameters through the input unit 28 of the console 14 enables the X-ray control parameters to be set in the X-ray controller 18 and the console control parameters to be set in the controller 26 of the console 14, and the controller 26 of the console 14 can make a judgment as to the validity of the X-ray control parameters, i.e., whether the X-ray control parameters are settable values, without inquiring of the X-ray controller 18 and inform the user of the judgment.

Accordingly, the X-ray imaging system 10 enables simplification of the imaging operations and improvement in imaging efficiency. Further, the X-ray imaging system of the invention can shorten the time required to complete image acquisition, i.e., the time during which the subject is required to wait until X-ray image acquisition is completed and reduce the strain on the subject.

Although the third setting range information is held in the X-ray controller 18 according to the above description, the third setting range information need not be held in the X-ray controller 18 when the judgments at the time of power-on and image acquisition are not made.

Next, a second embodiment of the X-ray imaging system of the invention will be described.

Figure 3:
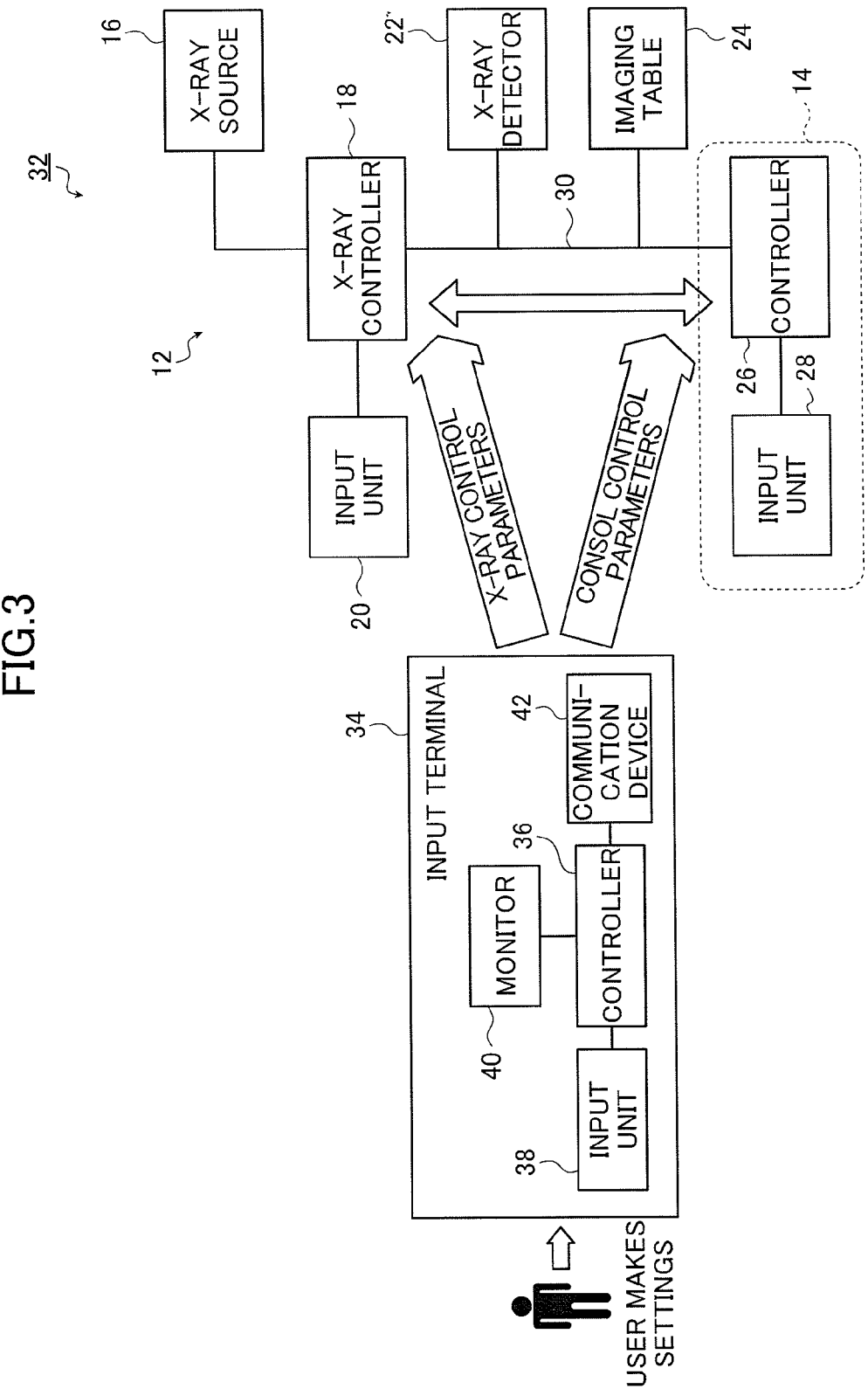
FIG. 3 is a block diagram illustrating a second embodiment representing a configuration of the X-ray imaging system of the invention.

FIG. 3 is a block diagram illustrating a second embodiment representing a configuration of the X-ray imaging system of the invention. An X-ray imaging system 32 illustrated in that figure comprises the imaging apparatus 12, the console 14, and an input terminal 34. In the description to follow, the same components as those of the X-ray imaging system 10 according to the first embodiment are given the same reference characters, of which a detailed description thereof will be omitted.

The X-ray controller 18 controls the operation of the X-ray source 16 according to the X-ray control parameters that are set when the values of the entered X-ray control parameters are judged by the input terminal 34 to be settable values.

The input unit 28 is an input means for entering various information in the controller 26. Although this embodiment does not use the input unit 28, the input unit 20 may be used to enter the console control parameters.

The controller 26 controls the operation of the entire X-ray imaging system according to the console control parameters that are set when the values of the entered console control parameters are judged by the input terminal to be settable values.

The input terminal 34 is a portable terminal easy to carry and comprises a controller 36 and an input unit 38 thereof, a monitor 40, and a communication device 42. The input terminal 34 may be, for example, a portable personal computer.

The input unit 38 is an input means for entering various information including the X-ray control parameters and the console control parameters in the controller 36.

The controller 36 holds the first setting range information representing an allowable range of values of the X-ray control parameters and the second setting range information representing an allowable range of values of the console control parameters. The controller makes a judgment as to whether the values of the X-ray control parameters entered through the input unit 38 are settable values according to the first setting range information and makes a judgment as to whether the console control parameters entered through the input unit 38 are settable values according to the second setting range information and informs the user of these judgments. The controller 36 sets the entered X-ray control parameters in the X-ray controller 18 when they are judged to be settable values, and sets the entered console control parameters in the controller 26 of the console 14 when they are judged to be settable values.

Under the control by the controller 36, the monitor 40 displays various information including the X-ray control parameters and the console control parameters entered through the input unit 38, the X-ray control parameters set in the X-ray controller 18 and the console control parameters set in the controller 26 of the console 14, and the judgments given by the controller 36.

Under the control by the controller 36, the communication device 42 transmits the X-ray control parameters to the X-ray controller 18 via wired communication or wireless communication Next, the operation of the X-ray imaging system 32 will be described.

In the description to follow, it is supposed that the third setting range information, which is original information of the first setting range information, is held in the X-ray controller 18, and fourth setting range information, which is original information of the second setting range information, is held in the controller 26 of the console 14.

Figure 4:
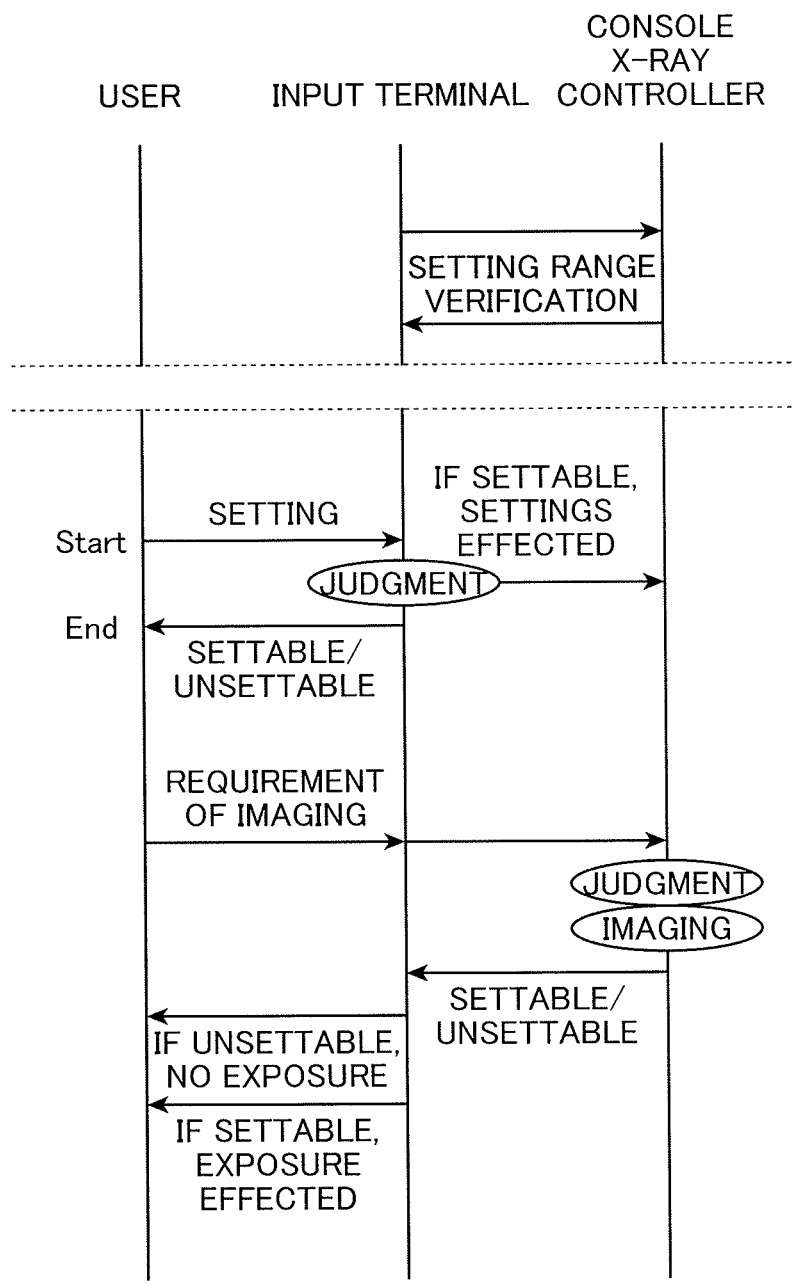
FIG. 4 is a conceptual view illustrating an operation of the X-ray imaging system of FIG. 3.
Figure 5:
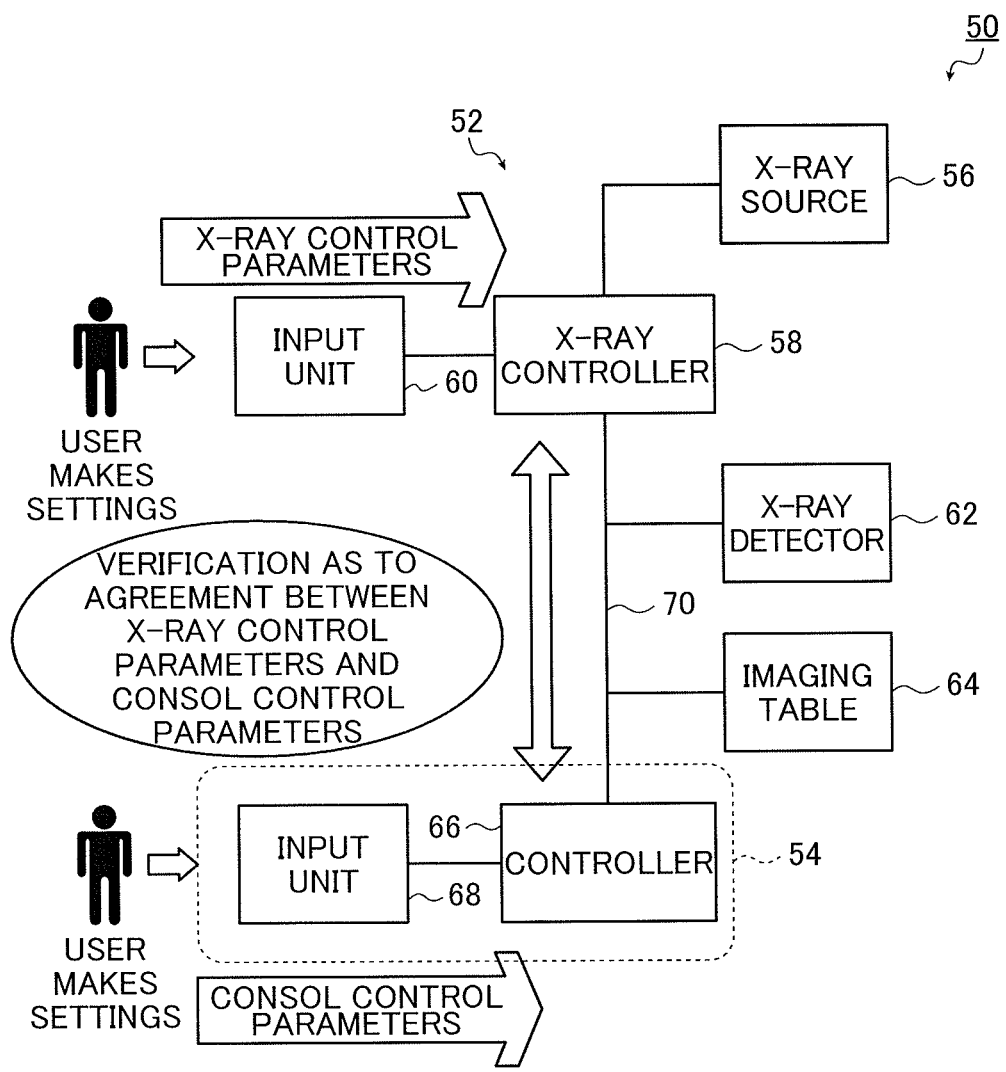
FIG. 5 is a block diagram illustrating an example of a configuration of a conventional X-ray imaging system.

As illustrated in FIG. 4 showing a concept of the operation, when, for example, the power of the X-ray imaging system 10 is turned on every morning, first the controller 36 of the input terminal 34 judges whether the values of the first setting range information held in the controller 36 and the values of the third setting range information held in the X-ray controller 18 agree (setting range verification). When they are judged to disagree, the values of the first setting range information are reset to the same values as the values of the third setting range information. Further, a judgment is made as to whether the values of the second setting range information held in the controller 36 and the values of the fourth setting range information held in the controller 26 of the console 14 agree (setting range verification). When they are judged to disagree, the values of the second setting range information are reset to the same values as the values of the fourth setting range information.

This ensures that even when the first setting range information and the second setting range information held in the controller 36 of the input terminal 34 have become unsettable values for some reason, the values are renewed and corrected each time the power is turned on and thus an inappropriate X-ray exposure may be prevented.

Then, the user (e.g., an X-ray imaging technician) enters (sets) the console control parameters and the X-ray control parameters in the X-ray imaging system 10 through the input unit of the input terminal 34.

Upon entry of the console control parameters and the X-ray control parameters, the controller 36 of the input terminal 34 judges whether the values of the entered X-ray control parameters are settable values according to the first setting range information and judges whether the values of the entered console control parameters are settable values according to the second setting range information.

When the controller 36 judges the values of the entered X-ray control parameters to be settable values, the user is informed that the values are settable values (SETTABLE), and the entered X-ray control parameters are set in the X-ray controller 18. When the values of the entered console control parameters are judged to be settable values, the user is informed that the values are settable values (SETTABLE), and the entered console control parameters are set in the controller 26 of the console 14.

When, on the other hand, the controller 36 judges the values of the entered X-ray control parameters to be unsettable values, the user is informed that the values are unsettable values (UNSETTABLE), and the user repeats the operation starting with the entry of the X-ray control parameters. When the controller 36 judges the values of the entered console control parameters to be unsettable values, the user is informed that the values are unsettable values (UNSETTABLE), and the user repeats the operation starting with the entry of the console control parameters.

When informed that both the X-ray control parameters and the console control parameters are settable values, the user pushes the exposure button (requirement of image acquisition).

Upon push of the exposure button, the X-ray controller 18 makes a judgment as to whether the X-ray control parameters set by the controller 36 of the input terminal 34 are settable values according to the third setting range information before and preferably immediately before X-ray image acquisition, and the user is informed of the judgment. When the values are judged to be unsettable values (UNSETTABLE), X-ray exposure is stopped. The controller 26 of the console 14 makes a judgment as to whether the console control parameters set by the controller 36 of the input terminal 34 are settable values according to the fourth setting range information, and the user is informed of the judgment. When the values are judged to be unsettable values (UNSETTABLE), X-ray exposure is stopped.

This ensures than even when the values of the X-ray control parameters set in the controller 18 and the values of the console control parameters set in the controller 26 of the console 14 have become unsettable values for some reason, an inappropriate X-ray exposure may be prevented by detecting that fact before image acquisition.

When, on the other hand, the values are judged to be settable (SETTABLE), the operation of the pertinent components is controlled by the controller 26 of the console 14 according to the console control parameters while the operation of the X-ray source 16 is controlled by the X-ray controller 18 according to the X-ray control parameters, causing the X-ray source 16 to irradiate the subject with X-ray. Then, the X-ray transmitted through the subject positioned by the imaging table 24 is detected by the X-ray detector 22 to acquire an X-ray image. The image signal of the acquired X-ray image is entered in the controller 26 of the console 14 and undergoes image processing and the like.

With the X-ray imaging system 32, merely entering the X-ray control parameters and the console control parameters through the input unit of the input terminal 34 enables the X-ray control parameters to be set in the X-ray controller 18 and the console control parameters to be set in the controller 26 of the console 14, and the controller of the console 34 makes a judgment as to the validity of the X-ray control parameters and the console control parameters, i.e., as to whether the X-ray control parameters and the console control parameters are settable values, without inquiring of the X-ray controller 18 and the controller 26 of the console 14 and informs the user of the judgments.

Accordingly, also the X-ray imaging system 32 enables simplification of the imaging operations and improvement in imaging efficiency. Further, the time required to complete image acquisition, i.e., the time during which the subject is required to wait, can be shortened and the strain on the subject can be reduced.

Although the third setting range information is held in the X-ray controller 18 and the fourth setting range information is held in the controller 26 of the console 14 according to the above description, such information need not be held when the judgments at the time of power-on and image acquisition are not made.

The present invention is basically as described above.

The present invention, described above in detail, is not limited in any manner to the above embodiments and various improvements and modifications may be made without departing from the spirit of the invention.

We claim:

1. An X-ray imaging system comprising:
an X-ray source for radiating X-ray;
a console for controlling an operation of the X-ray imaging system in its entirety;
wherein the console comprising:
an input unit for entering X-ray control parameters, which are information for controlling an operation of the X-ray source; and
a controller holding first setting range information representing an allowable range of values of the X-ray control parameters, the controller making a judgment as to whether the values of the X-ray control parameters entered through the input unit are settable values according to the first setting range information and informing a user of the console of the judgment,
an X-ray controller for controlling an operation of the X-ray source according to X-ray control parameters that are set when the values of the entered X-ray control parameters are judged by the controller of the console to be settable values; and
an X-ray detector for detecting X-ray radiated from the X-ray source and transmitted through a subject and thereby outputting an image signal of an X-ray image of the subject,
wherein the X-ray controller holds third setting range information, which is original information of the first setting range information, and
wherein the console judges upon power-on whether values of the first setting range information agree with values of the third setting range information and, when these values are judged to disagree, resets the values of the first setting range information to same values as the values of the third setting range information.

2. The X-ray imaging system according to claim 1, wherein, when the values of the entered X-ray control parameters are judged to be settable values, the controller sets the entered X-ray control parameters in the X-ray controller for controlling an operation of the X-ray source.

3. The X-ray imaging system according to claim 1, wherein the input unit is further used to enter console control parameters, which are information for controlling an operation of the console, and
wherein the controller further holds second setting range information representing an allowable range of values of the console control parameters, the controller making a judgment as to whether the values of the console control parameters entered through the input unit are settable values according to the second setting range information and informing a user of the console of the judgment.

4. The X-ray imaging system according to claim 3, wherein, when the values of the entered console control parameters are judged to be settable values, the controller sets the entered console control parameters in the controller.

5. An X-ray imaging system comprising:
an X-ray source for radiating X-ray;
a console for controlling an operation of the X-ray imaging system in its entirety;
wherein the console comprising:
an input unit for entering X-ray control parameters, which are information for controlling an operation of the X-ray source; and
a controller holding first setting range information representing an allowable range of values of the X-ray control parameters, the controller making a judgment as to whether the values of the X-ray control parameters entered through the input unit are settable values according to the first setting range information and informing a user of the console of the judgment,
an X-ray controller for controlling an operation of the X-ray source according to X-ray control parameters that are set when the values of the entered X-ray control parameters are judged by the controller of the console to be settable values; and
an X-ray detector for detecting X-ray radiated from the X-ray source and transmitted through a subject and thereby outputting an image signal of an X-ray image of the subject,
wherein the X-ray controller holds third setting range information, which is original information of the first setting range information, and makes a judgment as to whether the values of the set X-ray control parameters are settable values according to the third setting range information before the X-ray image of the subject is acquired, and a user of the X-ray imaging system is informed of the judgment.

6. The X-ray imaging system according to claim 5, wherein, when the X-ray controller judges that the values of the set X-ray control parameters are unsettable values, the X-ray controller does not allow the X-ray source to radiate X-ray.

7. The X-ray imaging system according to claim 5, wherein, when the values of the entered X-ray control parameters are judged to be settable values, the controller sets the entered X-ray control parameters in the X-ray controller for controlling an operation of the X-ray source.

8. The X-ray imaging system according to claim 5, wherein the input unit is further used to enter console control parameters, which are information for controlling an operation of the console, and
wherein the controller further holds second setting range information representing an allowable range of values of the console control parameters, the controller making a judgment as to whether the values of the console control parameters entered through the input unit are settable values according to the second setting range information and informing a user of the console of the judgment.

9. The X-ray imaging system according to claim 8, wherein, when the values of the entered console control parameters are judged to be settable values, the controller sets the entered console control parameters in the controller.

10. An X-ray imaging system comprising:
an X-ray source for radiating X-ray;
an input terminal;
   wherein the input terminal comprising:
   an input unit for entering X-ray control parameters, which are information for controlling an operation of the X-ray source, and console control parameters, which are information for controlling an operation of a console for controlling an operation of the X-ray imaging system in its entirety; and
   a controller for holding first setting range information representing an allowable range of values of the X-ray control parameters and second setting range information representing an allowable range of values of the console control parameters, the controller making a judgment as to whether the values of the X-ray control parameters entered through the input unit are settable values according to the first setting range information, making a judgment as to whether the values of the console control parameters entered through the input unit are settable values according to the second setting range information, and informing a user of the input terminal of these judgments,
a console for controlling an operation of the X-ray imaging system in its entirety according to the console control parameters that are set when the values of the entered console control parameters are judged by the input terminal to be settable values;
an X-ray controller for controlling an operation of the X-ray source according to X-ray control parameters that are set when the values of the entered X-ray control parameters are judged by the input terminal to be settable values; and
an X-ray detector for detecting X-ray radiated from the X-ray source and transmitted through a subject and thereby outputting an image signal of an X-ray image of the subject,
wherein the X-ray controller holds third setting range information, which is original information of the first setting range information, and
wherein the input terminal judges upon power-on whether values of the first setting range information agree with values of the third setting range information and, when these values are judged to disagree, resets the values of the first setting range information to same values as the values of the third setting range information.

11. The X-ray imaging system according to claim 10, wherein the input terminal is a portable terminal carried between a plurality of imaging rooms and holds first setting range information and second setting range information corresponding to respective imaging rooms, and wherein, when the input terminal is used in the respective rooms, the input terminal informs a user using the input terminal of judgments made according to the first setting range information and the second setting range information corresponding to the respective imaging rooms.

12. The X-ray imaging system according to claim 10, further comprising:
a plurality of input terminals owned by individual users; and
wherein, when the X-ray imaging system is used, the input terminals owned by the individual users set the X-ray control parameters in the X-ray controller and set the console control parameters in the controller.

13. The X-ray imaging system according to claim 10, further comprising:
the input terminal shared by a plurality of users; and
wherein, when individual users use the X-ray imaging system, the input terminal sets X-ray control parameters corresponding to a user using the X-ray imaging system in the X-ray controller and sets console control parameters corresponding to a user using the X-ray imaging system in the console.

14. The X-ray imaging system according to claim 10, wherein, when the controller judges the values of the entered X-ray control parameters to be settable values, the controller sets the entered X-ray control parameters in the X-ray controller for controlling an operation of the X-ray source.

15. The X-ray imaging system according to claim 10, wherein, when the controller judges the values of the entered console control parameters to be settable values, the controller sets the entered console control parameters in the console.

* * * * *